(12) United States Patent
Trojer et al.

(10) Patent No.: US 8,727,095 B2
(45) Date of Patent: May 20, 2014

(54) CONVEYOR EQUIPMENT

(75) Inventors: Andreas Trojer, Vienna (AT); Dirk Blondiau, Vienna (AT); Michael Matheisl, Vösendorf (AT); Paul Sailer, Vienna (AT)

(73) Assignee: Inventio AG, Hergiswil (CH)

( * ) Notice: Subject to any disclaimer, the term of this patent is extended or adjusted under 35 U.S.C. 154(b) by 187 days.

(21) Appl. No.: 13/332,569

(22) Filed: Dec. 21, 2011

(65) Prior Publication Data
US 2013/0020174 A1 Jan. 24, 2013

(30) Foreign Application Priority Data

Dec. 22, 2010 (EP) .................................... 10196575

(51) Int. Cl.
*B66B 23/00* (2006.01)
*B65G 43/02* (2006.01)
(52) U.S. Cl.
USPC ........................... 198/323; 198/804; 198/322
(58) Field of Classification Search
None
See application file for complete search history.

(56) References Cited

U.S. PATENT DOCUMENTS 6,112,166 A * 8/2000 Joosten .......................... 702/185
6,988,607 B2 * 1/2006 Blondiau et al. .............. 198/322
7,864,067 B2 * 1/2011 Smith ............................ 340/676

* cited by examiner

*Primary Examiner* — Kavel Singh
(74) *Attorney, Agent, or Firm* — Ladas & Parry LLP

(57) ABSTRACT

A handrail with handrail elements is moved past a sensor support with at least one sensor. Each handrail element has, for example, a collar, which extends into the adjacent handrail element. The handrail elements, which are pivotably fastened to a second transport chain, can move relative to the adjacent handrail elements without a gap then arising between two adjacent handrail elements. Merely a segment groove with such a small depth that fingers are not caught arises between two adjacent handrail elements. The sensor can recognize each segment groove as well as defective handrail elements. Operating magnitudes such as speed, acceleration and deceleration of the handrail are ascertainable and/or risk-laden operating states are recognizable by means of the sensor signal.

14 Claims, 6 Drawing Sheets

CONVEYOR EQUIPMENT

CROSS-REFERENCE TO RELATED APPLICATION

This application claims priority to European Patent Application No. 10196575.4, filed Dec. 22, 2010, which is incorporated herein by reference.

FIELD

The disclosure relates to conveyor equipment.

BACKGROUND

Person conveyor equipment with a handrail has become known from the specification WO 2004/014774, wherein at least one transponder is integrated in the handrail. A communications device arranged in the vicinity of the handrail comprises a transmitter and a receiver. The transmitter transmits energy and data in the form of electromagnetic waves to the transponder. The transponder transmits measurement data of physical parameters such as, for example, temperature or speed or acceleration of the handrail to the receiver. Transponders integrated in the handrail can be suitable for band-like or belt-like handrails. Such handrails can, for example, be monitored by a few pairs of transponders.

SUMMARY

In at least some embodiments, metallic or non-metallic conveyor elements of an endless conveyor are detectable. The conveyor elements to be detected are, for example, handrail elements, wherein a handrail can also consist of one handrail element, steps, pallets or chain elements. The conveyor elements form a segmented endless conveyor, for example a handrail, a step belt, a pallet belt or a transport chain for the steps or the pallets or the handrail elements. In further embodiments, the sensor necessary for detection of the conveyor elements detects the conveyor elements at a very short distance. The monitoring equipment can thereby be of compact and slender construction. The monitoring equipment detects each individual conveyor element and generates therefrom operating magnitudes such as, for example, speed and/or acceleration/deceleration. Missing or damaged conveyor elements are also detectable. In this case the endless conveyor concerned is stopped and/or an alarm concerning the fault given. The monitoring equipment can also be suitable for counting conveyor elements forming the segmented endless conveyor.

BRIEF DESCRIPTION OF THE DRAWINGS

The disclosed technologies are explained in more detail by way of the following detailed description and the accompanying figures, in which.

DETAILED DESCRIPTION

An exemplifying embodiment of conveyor equipment for persons and/or objects with conveyor elements combined to form endless conveyors is explained in the following on the basis of an escalator with handrail, step belt and transport chains. The explanations also apply analogously to a moving walkway with pallets or a conveyor belt. In the case of an escalator a conveyor element is a handrail element, wherein a handrail element can also consist of one handrail element, or is a step or a chain element. The handrail elements form the handrail, the steps form the step belt and the chain elements form the transport chains of the step belt. In the case of a moving walkway a conveyor element is a handrail element, a pallet or a chain element. The handrail elements form the handrail, the pallets form the pallet belt and the chain elements form the transport chains of the pallet belt or of the handrail.

Figure 1:
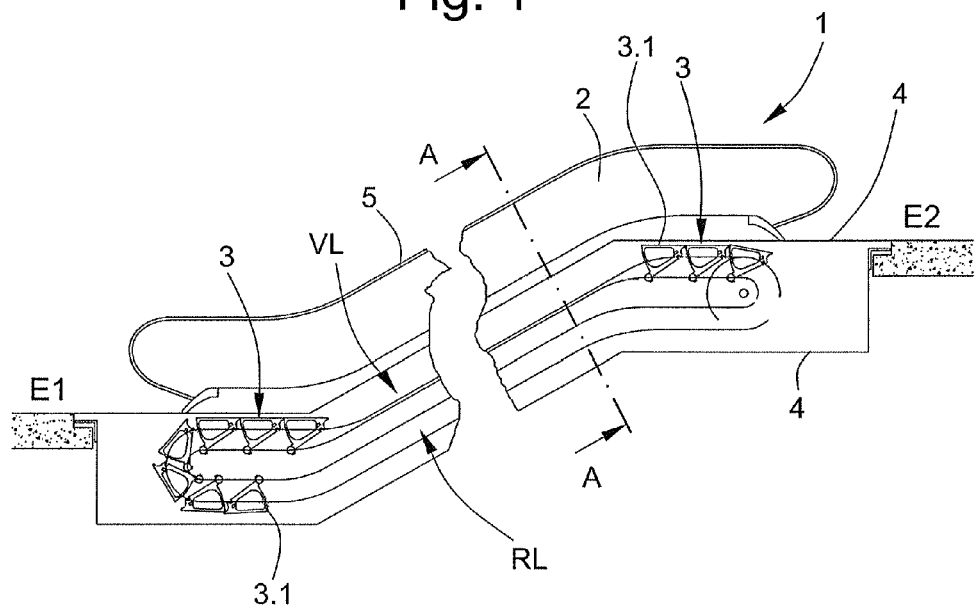
FIG. 1 shows, by way of example, conveyor equipment for persons and/or objects.

FIG. 1 schematically shows conveyor equipment in the example of an escalator 1 with a balustrade 2 and with a step belt 3 with steps 3.1 for the transport of persons and/or objects in the forward run VL from a first story E1 to a second story E2 or conversely. The endless step belt 3 moves back in the return run RL. A framework 4 serves as support for the step belt 3 and the balustrade 2 and is supported at the stories E1, E2. A handrail 5 carried by the balustrade 2 serves in the forward run VL as an endless conveyor for the hands of the persons to be transported.

Figure 2:
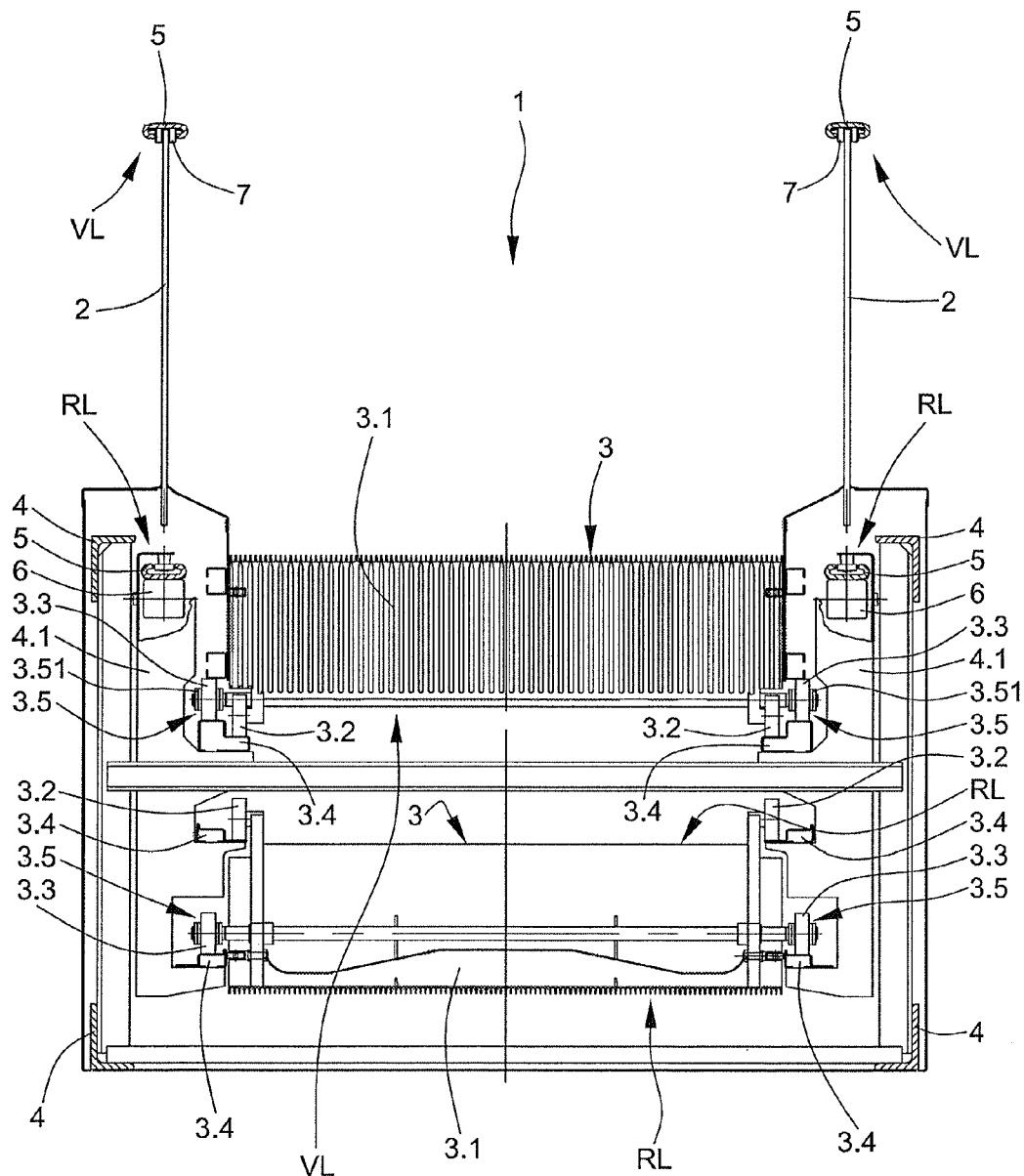
FIG. 2 shows a section through the conveyor equipment of FIG. 1 along the line A-A.

FIG. 2 shows a section through the conveyor equipment of FIG. 1 along the line A-A. Each step 3.1 has step rollers 3.2 and chain rollers 3.3, wherein the rollers 3.2, 3.3 roll along guides 3.4. The guides are arranged at frames 4.1 of the framework 4. A first transport chain 3.5 with chain elements 3.51 transports, as an endless conveyor, the steps 3.1 in the forward run VL and in the return run RL. The handrail 2 is guided in the return run RL by means of return run rollers 6 and in the forward run VL by means of a first guide profile member 7.

Figure 3:
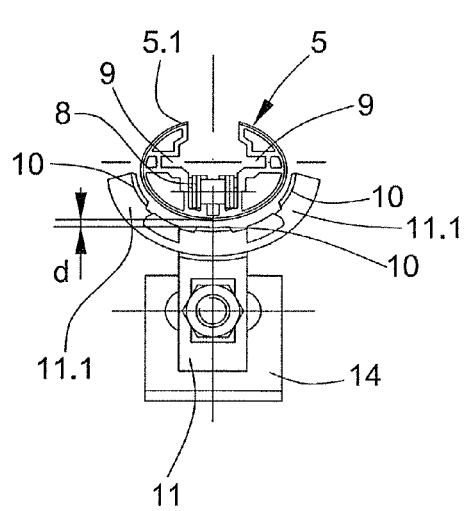
FIG. 3 shows a cross-section through a handrail in the return run.

FIG. 3 shows a cross-section through a handrail 5 in the return run RL, wherein the handrail 5 is constructed from individual handrail elements 5.1 in the manner of, for example, hollow bodies. The handrail elements 5.1 are transported by means of a second transport chain 8 and are guided at guide grooves 9 along the first guide profile member 7 of the balustrade 2. A yoke 11 is fastened to a bracket 14 by means of a screw 12 and nut 13, wherein, for example, a sensor support 11.1 with sensors 10 for monitoring the handrail elements 5.1 is arranged at the yoke 11. The sensor support 11.1 is equipped with three sensors 10, but it can also be provided with only two sensors or only one sensor.

Figure 4:
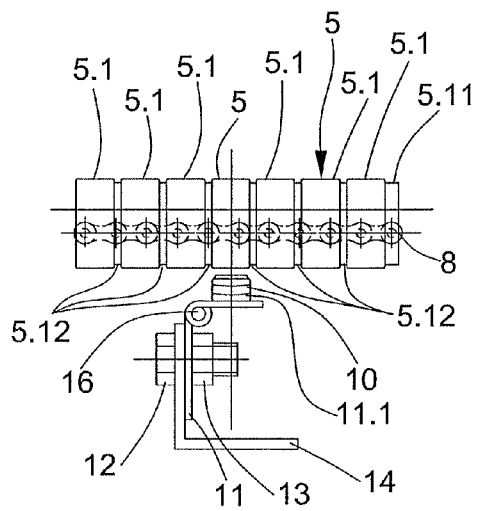
FIG. 4 shows a side view of the handrail according to FIG. 3.

FIG. 4 shows a side view of the handrail 5 according to FIG. 3, wherein the handrail elements 5.1 are moved past the sensor support 11.1. For the sake of better clarity of the monitored handrail element 5.1 the sensor support 11.1 shown in FIG. 3 is not fully illustrated in FIGS. 4 to 6. A joint 16 is provided at the yoke 11, wherein a damaged handrail element 5.1 pivots, by protruding parts, the sensor support 11.1 away, in which case the sensors 10 remain intact. Each handrail element 5.1 has a collar 5.11 which extends into the adjacent handrail element 5.1. The handrail elements 5.1, which are pivotably fastened to the second transport chain 8, can move relative to the adjacent handrail elements 5.1 without a gap then arising between two adjacent handrail elements 5.1. Merely a segment groove 5.12, with such a small depth that fingers are not caught, arises between two adjacent handrail elements 5.1. The segment groove 5.12 has, for example, a depth of approximately 2 millimeters to 4 millimeters and a width of approximately 4 millimeters to 8 millimeters.

Figure 5:
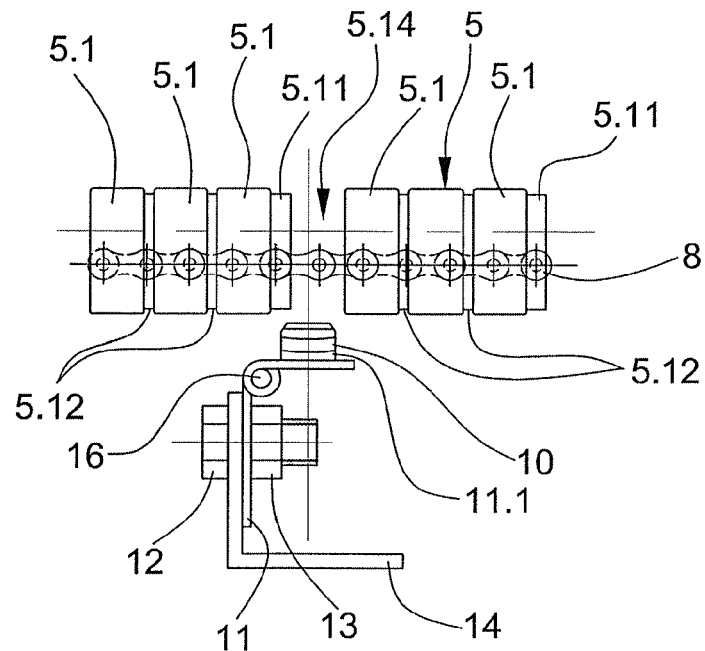
FIG. 5 shows a handrail with a missing handrail element.

FIG. 5 shows the handrail 5 with a missing handrail element 5.1. A handrail element 5.1 has, for example, been broken and dropped off or forcibly removed by vandals. The sensors 10 detect every present and also every missing handrail element 5.1.

Figure 6:
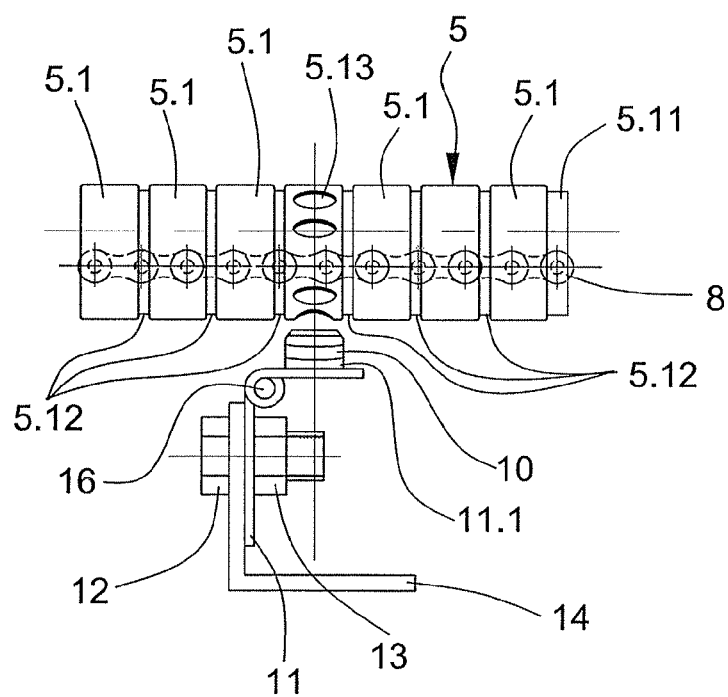
FIG. 6 shows the handrail with a damaged handrail element.

FIG. 6 shows the handrail 5 with a damaged handrail element 5.1. In the case of a handrail element 5.1, for example, parts have been broken out or forcibly removed by vandalism. The sensors 10 detect every present and also every damaged handrail element 5.1. Damaged handrail elements 5.1 have, for example, craters, tears and/or holes 5.13.

Sensors 10 functioning on different principles of operation come into question according to the material characteristics of the conveyor elements. Suitable for monitoring of a segmented handrail 5 formed from handrail elements 5.1 or for monitoring of a step/pallet belt 3 formed from steps 3.1 or pallets or for monitoring a first transport chain 3.5 or a second transport chain 8 formed from chain elements 3.51 are, for example, antennae 10.1 having a radiation characteristic variable by the proximity to the antenna and by the segmentation of the handrail 5 or of the step/pallet belt 3 or of the transport chains 3.5, 8, as explained below in detail. Sensors operating on the principle of radar also come into question, wherein an antenna transmits electromagnetic signals to the endless conveyors with conveyor elements, the signals are reflected depending on the contour of the endless conveyor and the reflected signals are measured. Sensors operating on the capacitive principle are also possible. In that case the capacitance of a capacitor is changed by the segmentation of the endless conveyor. The capacitor forms, together with an inductance, an oscillator circuit, the resonance frequency of which changes in dependence on the capacitor capacitance and determines the frequency of an oscillator.

In the following, a sensor 10 with an antenna 10.1 is explained in more detail, the radiation characteristic of which is variable by the proximity to the antenna and by the segmentation 5.12 of an endless conveyor such as, for example, a handrail 5, a step/pallet belt 3 or a transport chain 3.5, 8.

A small spacing, for example in the near field of the antenna 10.1, between antenna 10.1 and conveyor elements such as, for example, handrail elements, steps/pallets, and chain elements, leads to disturbance signals which are superimposed on a desired useful signal. No interaction with objects arises in the far field; the antenna radiates freely, wherein the far field is determined as follows: $d/\lambda > 1$ ($d$=spacing of the antenna from the endless conveyor, $\lambda$=wavelength of the signal radiated by means of the antenna). An object in the near field detunes the antenna and changes the resistance thereof, wherein the near field is determined as follows: $d/\lambda < 1$.

The spacing d of the antenna 10.1 from the handrail element 5.1 shown in FIG. 3 is, for example, fixed at 1.5 millimeters to 3.5 millimeters at a near field, in which tears with, for example, a length of approximately 5 millimeters and/or holes 5.13 with, for example, a diameter of approximately 5 millimeters are precisely detectable. Holes 5.13 and tears detune the antenna 10.1 less than bulges and protruding parts, for example, of the handrail 5. An antenna (10.1) operating in the ultra-high-frequency range is used as sensor (10), for example a commercially available 2.4 GHz WLAN antenna (WLAN signifies Wireless Local Area Network).

$\varepsilon_r$ is a material constant for conveyor elements and is greater than 1 ($\varepsilon_r$ for a vacuum equals 1). Intermediate spaces between the conveyor elements, for example the segment groove 5.12 between two adjacent handrail elements 5.1 or a slot between two adjacent steps or pallets or step-like transitions from one chain element 3.51 to the adjacent chain element 3.51, produce a sequence of changes of the dielectric constant $\varepsilon_r$. For example, in the case of the segmented handrail the sequence of handrail element—segment groove—handrail element—segment groove—handrail element . . . etc., is present in the segmented handrail, wherein a handrail element has a greater $\varepsilon_r$ than a segment groove ($\varepsilon_r$ nearer to 1).

In some embodiments, a change in the electrical field in the near field of the antenna 10.1 is usable. Changes in the dielectric constant $\varepsilon_r$ of the conveyor elements disposed in the immediate vicinity of the antenna 10.1, such as, for example, handrail elements, steps/pallets, chain elements, lead to a detuning of or to a change in the resonance frequency of the antenna 10.1. These changes produce an energy reflection which is measurable in the feed to the antenna.

Changes in the dielectric constant $\varepsilon_r$ in the immediate vicinity of the antenna 10.1 are caused by the conveyor elements led past the antenna.

At least some embodiments feature a compact construction of the antenna and a small spacing d of the antenna from the conveyor elements.

Figure 7:
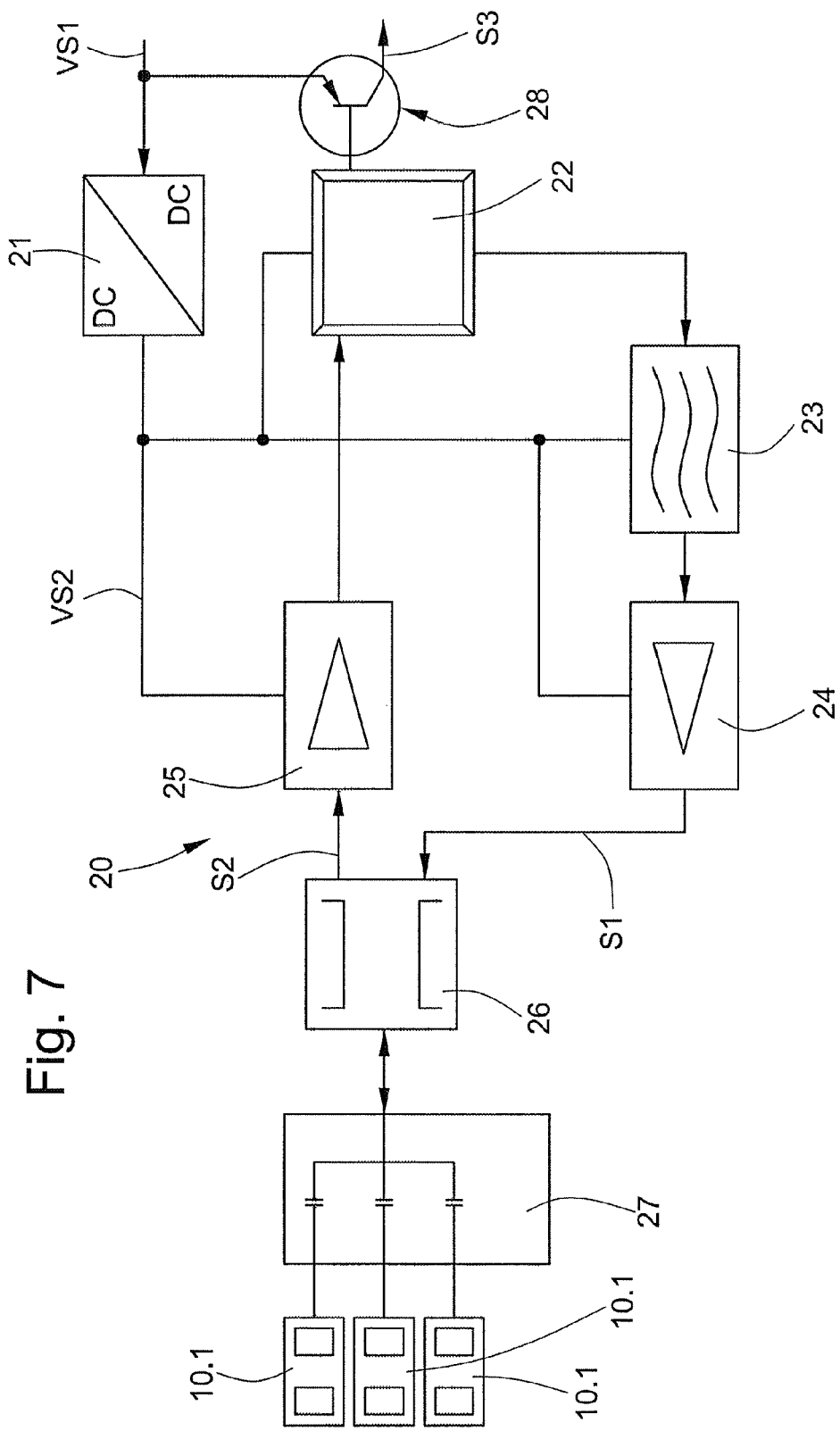
FIG. 7 shows a block circuit diagram of a circuit for monitoring an endless conveyor.

FIG. 7 shows a block circuit diagram of a circuit 20 for preparing the sensor signal produced by the sensor 10. A voltage converter 21 is supplied with a first supply voltage VS1, for example 24 volts of the escalator 1. The voltage converter 21 generates from the first supply voltage VS1 a second supply voltage VS2, for example 5 volts, with which a control 22, an oscillator 23, a ultra-high-frequency amplifier 24 and a measurement value amplifier 25 are supplied.

The control 22 presets a frequency corresponding with the antenna 10.1, wherein the oscillator 23 generates a signal with this frequency and predetermined form and amplitude, for example a sine signal, and feeds it to the ultra-high-frequency amplifier 24. The amplified ultra-high-frequency signal S1 is fed to a measuring quadripole network 26 and by this to an antenna coupler 27 to which the antennae 10.1 arranged at the sensor support 11.1 are coupled. Without objects in the near field of the antenna 10.1 the antenna acts in purely ohmic manner (for example 50 ohms) and the full energy of the first signal S1 is radiated without reflection. If, as explained above, objects are located in the near field of the antenna 10.1, the resonance frequency of the antenna 10.1 is detuned by the interaction with the objects and a part of the energy of the first signal S1 is reflected by the antenna 10.1 to the measuring quadripole network 26 and appears as a second signal S2, which images the surface of the endless conveyor, at the measuring quadripole network 26. The second signal S2 is fed to the measurement value amplifier 25. This amplifies the second signal S2 and feeds it to the control 22 for evaluation.

If endless conveyors without contour or without damage locations, which are visible to the eye, at the surface or without elemental structure or without segmentation are moved past the antenna 10.1 in the near field of the antenna 10.1 a second signal S2, in particular, arises—here also termed 'disturbance signal'—but without 'useful signal'. The useful signal superimposed on the disturbance signal arises only with a change of the surface of the endless conveyor or with the contouring of the endless conveyor or with structures, which are visible to the eye, such has holes or tears or notches or slots, etc., at the surface or with the segment grooves 5.12 of the handrail elements 5.1 or with the slots between the steps or with the step-like transitions from one chain element to another, wherein the change of the surface of the endless conveyor produces a change in the radiation characteristic of the antenna.

Changes, which are visible to the eye, of the surface of the endless conveyor are recognizable by the sensor 10 just as, for example, segment grooves of the handrail elements, a non-segmented handrail provided with slots, a non-segmented handrail provided with tears, damaged handrail elements with holes and/or tears, missing handrail elements, missing steps or pallets, step-like transitions from one chain element to other, missing chain elements, protruding parts of the endless conveyor, slots between conveyor elements, etc.

Figure 8:
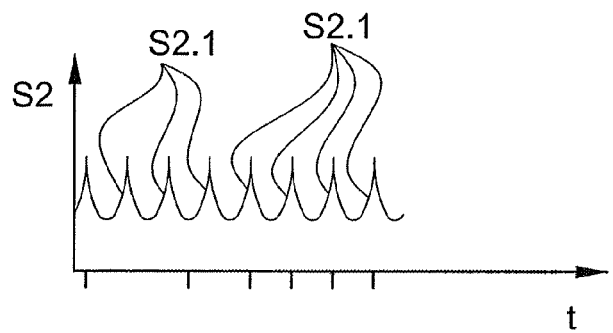
FIG. 8 shows an electrical image of a segmented handrail provided with handrail elements.

FIG. 8 shows an electrical image of a segmented handrail 5 according to FIG. 4 provided with handrail elements 5.1. The second signal S2 is illustrated as a function of time t. The intact handrail 5 moved past the antenna 10.1 generates, by each segment groove 5.12, a wave-shaped useful signal S2.1 superimposed on the disturbance signal, wherein each wave S2.1 is detected by the control 22.

In order to suppress disturbing effects a mean value is formed from the last-measured waves S2.1 (for example, from the last 64 measured waves) by the control 22 and the mean value is compared with the measurement value of the current wave S2.1. If the difference of the current measurement value from the mean value lies within a defined tolerance band, the currently measured handrail element 5.1 is treated as intact.

Figure 9:
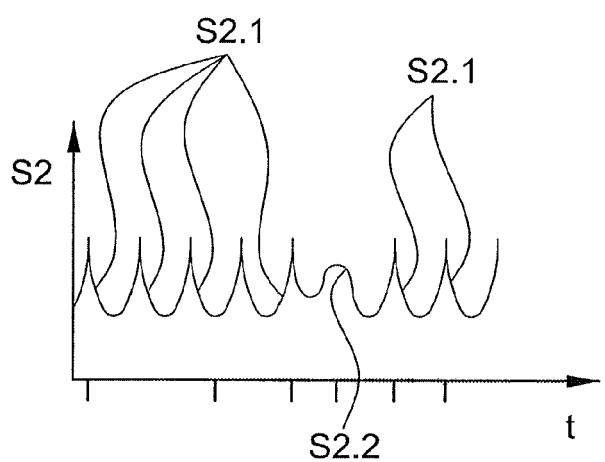
FIGS. 9 and 10 show an electrical image of a damaged handrail.

FIG. 9 shows an electrical image of a segmented handrail 5 according to FIG. 5, which is provided with handrail elements 5.1, with a missing handrail element 5.1. The second signal S2 is illustrated as a function of time t. The missing handrail element 5.1 forms the associated signal wave S2.2 only in stunted form. The control 22 recognizes the damaged location and generates a fault signal.

Figure 10:
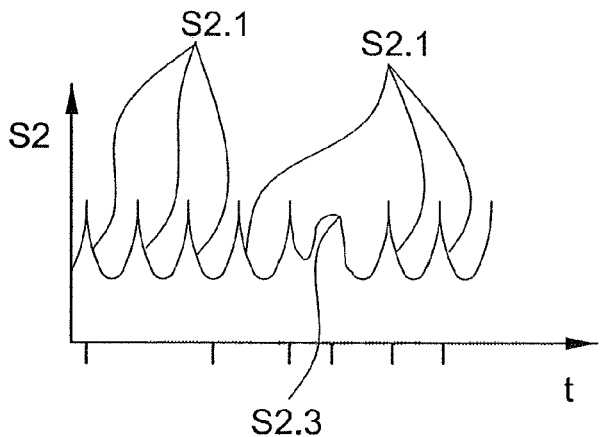

FIG. 10 shows an electrical image of a segmented handrail 5 according to FIG. 6, which is provided with handrail elements 5.1, with a handrail element 5.1 provided with holes 5.13 and/or tears. The second signal S2 is illustrated as a function of time t. The damaged handrail element 5.1 forms the associated signal wave S2.3 only in stunted form. The control 22 recognizes the damage location and generates a fault signal.

The control 22 of FIG. 7 generates, by means of an output stage 28, a third signal S3 corresponding with the operational state of the endless conveyor. The output stage can include, for example, a semiconductor switch, an optocoupler or a bus system.

Figure 11:
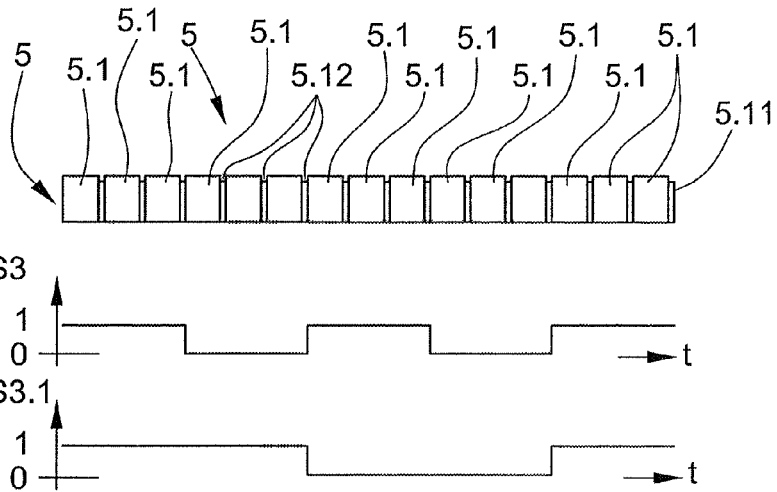
FIGS. 11 to 13 show output signals of the circuit in dependence on the operating state of the endless conveyor.

FIG. 11 shows an endless conveyor in the example of the segmented handrail 5 with handrail elements 5.1. The handrail generates at rated speed the illustrated signal S3 as a function of time t. The signal S3 changes, for example, after each third handrail element 5.1, from logic 0 to logic 1 and conversely. At, by way of example, half speed, the signal S3.1 is generated as a function of time t. The signal S3, S3.1 is, for example, fed to the escalator control for speed regulation and/or for speed monitoring. Operating magnitudes such as, for example, conveyor speed, acceleration when starting off or retardation when coming to a stop are determined from the number of pulses per unit of time.

Figure 12:
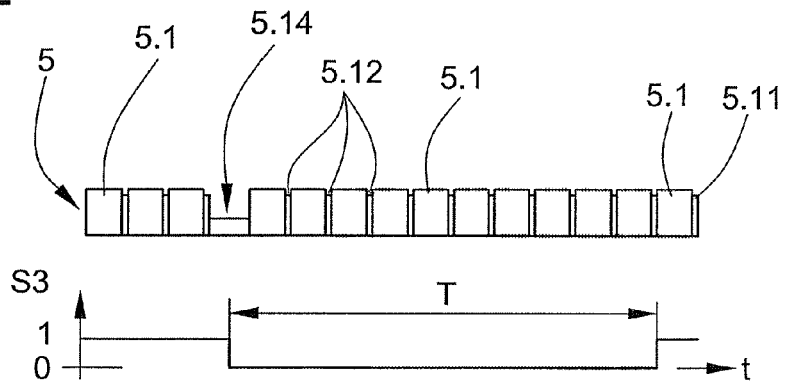

FIG. 12 shows the output signal S3 in the case of a partly or completely missing handrail element 5.14 or in the case of a handrail element 5.1 with tears and/or holes 5.13. The third signal S3 is set to logic 0 for a specific time t, for example 30 seconds. The escalator control recognizes this state and generates at least one corresponding fault report.

Figure 13:
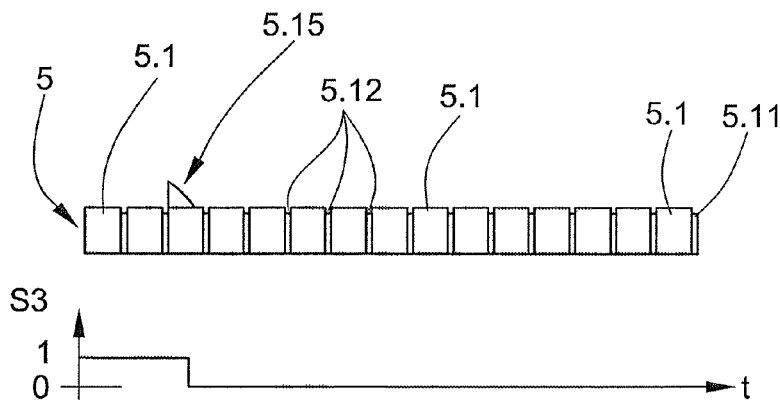

FIG. 13 shows the handrail 5 with a damaged handrail element 5.1 with protruding parts 5.15, which move the sensor support 11.1 away by way of the joint 16, in which case the sensors 10 remain intact. In the pivoted-away position the sensor cannot recognize handrail elements 5.1 and the signal S3 remains at logic 0. The escalator control recognizes this state, stops the escalator 1 and generates at least one corresponding fault report.

Having illustrated and described the principles of the disclosed technologies, it will be apparent to those skilled in the art that the disclosed embodiments can be modified in arrangement and detail without departing from such principles. In view of the many possible embodiments to which the principles of the disclosed technologies can be applied, it should be recognized that the illustrated embodiments are only examples of the technologies and should not be taken as limiting the scope of the invention. Rather, the scope of the invention is defined by the following claims and their equivalents. We therefore claim as our invention all that comes within the scope and spirit of these claims.

We claim:

1. Conveyor equipment, comprising:
   an endless conveyor, the endless conveyor comprising at least one conveyor element;
   at least one non-contact surface detection sensor for the endless conveyor; and
   a sensor signal imaging circuit coupled to the at least one surface detection sensor; the non-contact surface detection sensor comprising an antenna tuned to operate in an ultra-high frequency range, the at least one conveyer element being movable in a near field of the antenna, the sensor signal imaging circuit being responsive to changes in the near field of the antenna resulting from the presence of the conveyor element in the near field.

2. The conveyor equipment of claim 1, the at least one conveyor element comprising a segmented handrail.

3. The conveyor equipment of claim 1, the at least one conveyor element comprising a non-segmented handrail.

4. The conveyor equipment of claim 1, a spacing of the antenna from the at least one conveyor element being approximately 1.5 millimeters to 3.5 millimeters.

5. The conveyor equipment of claim 1, the antenna comprising a wireless local area network (WLAN) antenna.

6. The conveyor equipment of claim 5, the antenna being tuned for 2.4 GHz.

7. The conveyor equipment of claim 1, the antenna being pivotably deflectable by one or more protruding parts of the at least one conveyor element.

8. A conveyor equipment monitoring method, comprising:
   positioning a non-contact sensor comprising an antenna tuned to operate in an ultra-high frequency range proximate a surface of an endless conveyor, the endless conveyor comprising at least one conveyor element, whereby the surface is within a near field of the antenna ; and
   analyzing, using a circuit, changes in the antenna near field generated by the surface of the endless conveyor.

9. The conveyor equipment monitoring method of claim 8, the sensor comprising an antenna operating in an ultra-high-frequency range.

10. The conveyor equipment monitoring method of claim 9, further comprising:

sending an ultra-high-frequency signal from the circuit to the antenna; and sending a reflected signal from the antenna to the circuit.

11. The conveyor equipment monitoring method of claim 10, further comprising generating, using the circuit and based on the reflected signal, an indication of an operating magnitude of the endless conveyor.

12. The conveyor equipment monitoring method of claim 11, the operating magnitude comprising of one or more of speed of the endless conveyor, acceleration of the endless conveyor, and deceleration of the endless conveyor.

13. The conveyor equipment monitoring method of claim 10, further comprising generating, using the circuit and based on the reflected signal, an indication of a risk-laden operating state of the endless conveyor.

14. The conveyer equipment monitoring method of claim 13, the risk-laden operational state comprising one or more of a missing conveyor element, a damaged conveyer element, and a protruding conveyor element.

* * * * *